United States Patent [19]
Ersfeld et al.

[11] Patent Number: 5,439,438
[45] Date of Patent: Aug. 8, 1995

[54] HEAT SHRINKABLE BANDAGE COVER

[75] Inventors: Dean A. Ersfeld, Maplewood, Minn.; Timothy C. Sandvig, Wodoville, Wis.; John F. Reed, Arden Hille; Paul E. Hansen, Lake Elmo, both of Minn.

[73] Assignee: Minnesota Mining and Manufacturing Company, St. Paul, Minn.

[21] Appl. No.: 188,647

[22] Filed: Jan. 28, 1994

Related U.S. Application Data

[63] Continuation of Ser. No. 703,038, May 17, 1991, abandoned, which is a continuation of Ser. No. 242,120, Sep. 9, 1988, abandoned.

[51] Int. Cl.$^6$ .............................................. A61F 5/00
[52] U.S. Cl. ......................................................... 602/3
[58] Field of Search .................... 602/3, 5, 6, 7, 8, 41, 602/44, 45, 50, 60, 61, 62

[56] References Cited

U.S. PATENT DOCUMENTS

| | | | |
|---|---|---|---|
| 2,581,561 | 1/1952 | Shaw | 128/DIG. 18 |
| 2,616,084 | 11/1952 | Shearer | 128/DIG. 18 |
| 2,910,763 | 11/1959 | Lauterbach | 128/DIG. 18 |
| 2,948,634 | 8/1960 | Furendal | 128/DIG. 18 |
| 3,027,336 | 3/1962 | Götz | 128/90 |
| 3,083,708 | 4/1963 | Gottfried | 128/DIG. 20 |
| 3,186,405 | 6/1965 | Bailey | 602/13 |
| 3,314,419 | 4/1967 | Quick | 128/90 |
| 3,329,143 | 7/1967 | Gordon | 128/82 |
| 3,467,086 | 9/1969 | Addison | 128/90 |
| 3,547,950 | 12/1970 | Gander | 128/90 |
| 3,692,023 | 9/1972 | Phillips | 128/90 |
| 3,747,125 | 7/1973 | Goldman | 128/82 |
| 3,785,374 | 1/1974 | Lipson | 128/82 |
| 3,944,688 | 3/1976 | Inman | |
| 3,972,323 | 8/1976 | Boricheski | 128/91 R |
| 4,043,326 | 8/1977 | Little | 128/82 |
| 4,076,921 | 2/1978 | Stol | 128/82 |
| 4,105,025 | 8/1978 | Wang | 128/90 |
| 4,139,003 | 2/1979 | Little | 128/82 |
| 4,224,935 | 9/1980 | Metelnick | 128/82 |
| 4,254,765 | 3/1981 | Brown | 128/82 |
| 4,301,603 | 11/1981 | Scott | 128/82 |
| 4,346,699 | 8/1982 | Little | 128/82 |
| 4,411,928 | 10/1983 | Baldwin | |
| 4,523,586 | 6/1985 | Couri | |
| 4,552,795 | 11/1985 | Hansen et al. | |
| 4,562,834 | 1/1986 | Bates | 128/82 |
| 4,578,307 | 3/1986 | Niki et al. | |
| 4,640,859 | 11/1985 | Hansen | 428/110 |
| 4,705,712 | 11/1987 | Cashaw | 428/152 |
| 4,768,501 | 9/1988 | George | |
| 5,025,052 | 6/1992 | Crater et al. | 524/104 |

FOREIGN PATENT DOCUMENTS

| | | |
|---|---|---|
| 0181300 | 5/1986 | European Pat. Off. . |
| 0260011 | 3/1988 | European Pat. Off. . |
| 0352095 | 1/1990 | European Pat. Off. . |
| 0358451 | 3/1990 | European Pat. Off. . |
| 0448883 | 10/1991 | European Pat. Off. . |
| 0494083 | 7/1992 | European Pat. Off. . |
| WO93/07914 | 4/1993 | WIPO . |

OTHER PUBLICATIONS

Derwent Abstract—JP 62 104 978.
PCT Search Report for PCT/US94/05417.
Asaki Kasai SMASH ® product literature.

*Primary Examiner*—Michael A. Brown
*Attorney, Agent, or Firm*—Gary L. Griswold; Walter N. Kirn; F. Andrew Ubel

[57] ABSTRACT

A protective covering of nonwoven fabric for an orthopedic cast, wound dressing or other bandage is disclosed. The covering is adapted to fit loosely about the bandage to be protected and is capable of being heat-shrunk at a relatively low temperature to closely cover the bandage. The covering is permeable to water vapor and air, it may be treated with a surface active agent to provide superior water and soil repellency, and it may be provided in various colors or with various decorative designs.

38 Claims, 3 Drawing Sheets

Fig. 5

HEAT SHRINKABLE BANDAGE COVER

This is a continuation of application Ser. No. 07/703,038 filed May 17, 1991 now abandoned, which is a continuation of Ser. No. 07/242,120 filed on Sep. 9, 1988 now abandoned.

FIELD OF THE INVENTION

This invention relates to coverings for orthopedic casts, wound dressings, wraps and other bandages. More particularly, it relates to such coverings which are heat shrinkable.

BACKGROUND OF THE INVENTION

There exists a need to cover dressings, wraps, casts and other bandages for aesthetic reasons and to protect them from soil and moisture. To this end, there are numerous simple coverings in common use which afford some degree of protection. Among the most common of these is a tubular knit sock which is pulled over the cast or wound dressing, and the common elastic bandage which is wrapped around the cast or wound dressing. While such coverings are suitable to protect the dressing from soil, they are inadequate to protect the dressing from water, since they are easily wetted.

A number of cast covers are known which are useful in reducing the wetting of a cast during bathing or other exposure to water. U.S. Pat. No. 4,523,586 discloses a loose fitting bag made of flexible material and adapted to fit over a cast and be sealed with fasteners around the casted limb. The cast is thus protected from water damage. Similarly, U.S. Pat. No, 4,346,699 discloses a balloon-like cast cover into which the casted limb is inserted and the neck of which is adapted to fit tightly about the casted limb above the cast. While these cast covers are impermeable to water, their usefulness is limited to short term exposure to water such as occurs during bathing. They are not suitable for extended wear because the escape of water vapor from the inside of the cast cover is prevented or impeded, evaporative cooling of the skin under the cast or dressing is prevented, and discomfort to the user results.

Disclosed in U.S. Pat. No. 4,552,795 is a heat-shrinkable sheet material formed by stretching elastomeric strands and then bonding them to one or more flat inelastic webs. When the sheet material is heated, the strands contract, the material shirrs, and an elastic laminate results. The flat inelastic webs may be porous and nonwoven, and a porous elastic wrap suitable for holding bandages in place is taught.

U.S. Pat. No. 3,329,143 discloses a tubular cast cover of highly plasticized heat-shrinkable polyvinyl chloride homopolymer or copolymer. The cover is adapted to thermally shrink to closely fit the contours of a cast upon exposure to temperatures of 60° C. to 82° C. Further, the cover is perforated to allow air and water permeability, although no method of perforation is described. This cast cover appears to be weak and easily torn, thus requiring frequent replacement by the user. Furthermore, the air and water permeability achieved by physical perforation of the covering may be inadequate since the permeability is not continuous throughout the covering and water may penetrate the covering through the holes and wet the cast.

SUMMARY OF THE INVENTION

According to the present invention, there is provided a protective covering for an orthopedic cast, wound dressing, or other bandage. The covering comprises one or more sheets of a nonwoven fabric of heat shrinkable fibers. The covering is adapted to fit loosely about the bandage and is capable of being heat-shrunk to closely cover the bandage.

Preferably, the fabric can be adequately heat-shrunk at temperatures below about 65° C. to minimize discomfort to the patient. Presently, the most preferred nonwoven fabric is made of oriented, melt-blown microfibers of a copolymer of terephthalic acid, ethylene glycol and diethylene glycol. The fabric is preferably embossed to maximize its strength and durability. It is also preferred to chemically treat the fabric with a surface active agent such as a fluorochemical formulation or a silicone formulation to impart a low surface energy ($<30$ erg/cm$^2$ or dyne/cm) which results in water and soil repellency.

The covering of the invention is permeable to moisture vapor and air and thus suitable for extended wear over a bandage. It is relatively strong and durable and it protects the underlying bandage from soil and water, especially when chemically treated. The covering is also aesthetically pleasing since it conforms closely to the bandage without sagging or wrinkling. Further, the covering can be provided in various colors or with various decorative designs, prints or patterns. Moreover, when worn over an orthopedic cast, the covering provides a smooth surface which protects clothing from damage that might otherwise be caused by rough areas on the surface of the cast.

The covering of the invention is easily removed with scissors or other simple cutting tools. It is easily replaced, and it is relatively inexpensive to manufacture. As a consequence, the covering of the invention may be considered by the user to be a disposable item suitable for frequent replacement.

Thus, the invention provides a disposable, breathable, water and soil repellent, soft, durable and attractive covering for an orthopedic cast, wound dressing or other bandage. Other advantages of the invention will be apparent from the following description.

BRIEF DESCRIPTION OF THE DRAWINGS

The invention will be better understood by reference to the drawings.

DETAILED DESCRIPTION OF THE INVENTION

The invention is a protective covering for an orthopedic cast, splint, wound dressing, wrap or other bandage used on the body (all of which are collectively termed bandages for present purposes). The covering is adapted to fit loosely over the bandage to be protected and is subsequently heat-shrunk to closely cover the bandage.

Figures 1, 2:
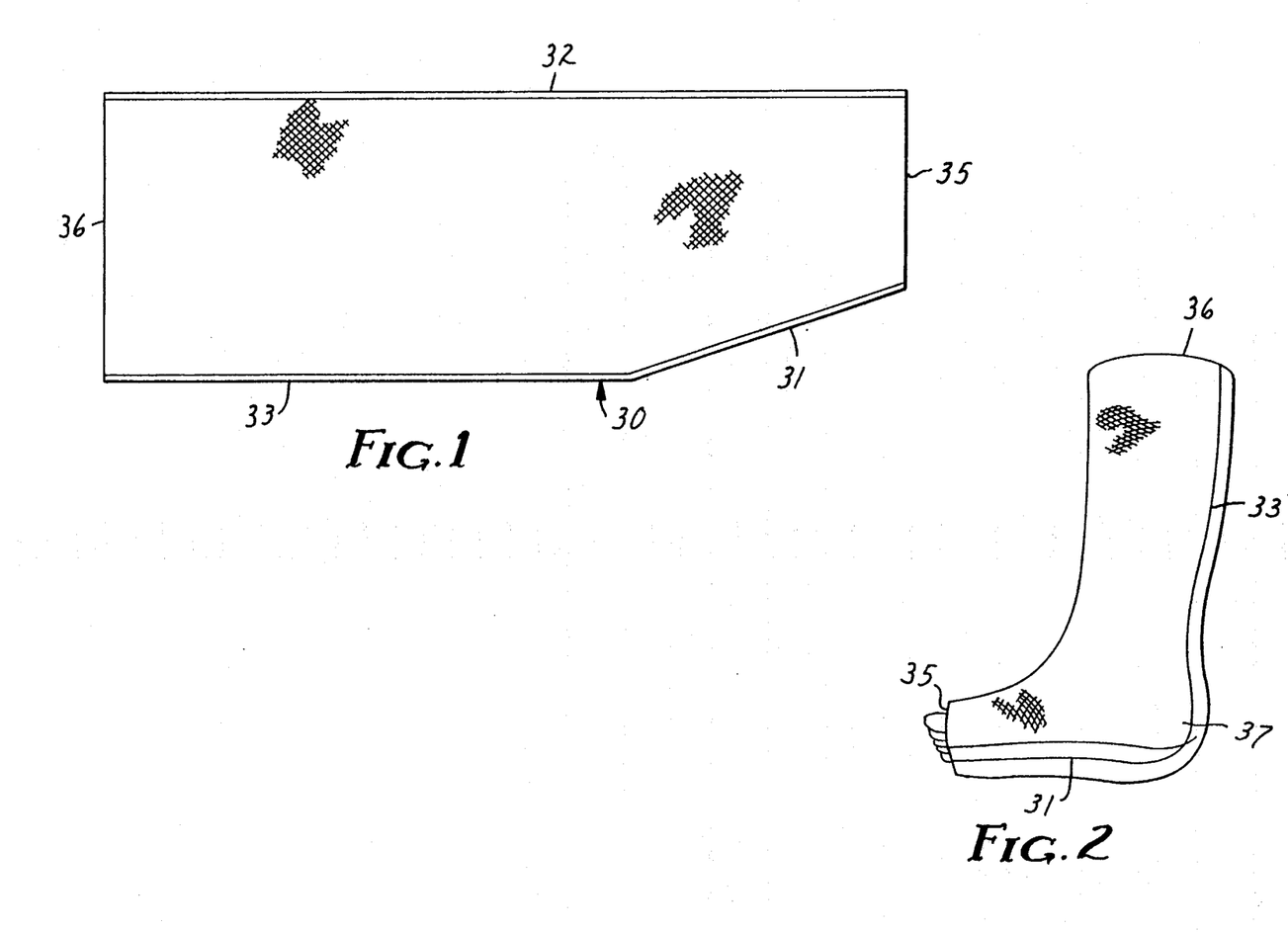
FIG. 1 is a plan view of one embodiment of the invention. This embodiment is a tapered tubular covering intended for use with a short leg cast.
FIG. 2 is a perspective view of the embodiment shown in FIG. 1, wherein the covering has been placed around a short leg cast and heat-shrunk to closely cover the cast.

With reference to the drawings, FIG. 1 depicts a tapered tubular bandage cover 30 comprising two matched sheets of nonwoven web. The sheets are heat sealed along the edges 31, 32 and 33, and the ends 35 and 36 are left open. FIG. 2 depicts the cover shown in FIG. 1 in place, having been heat-shrunk to closely cover a short leg cast. The seam along edge 31 of the cover is centered along the bottom of the foot portion 37 of the cast, and the open ends 35 and 36 are tucked into the ends of the cast.

Figure 3:
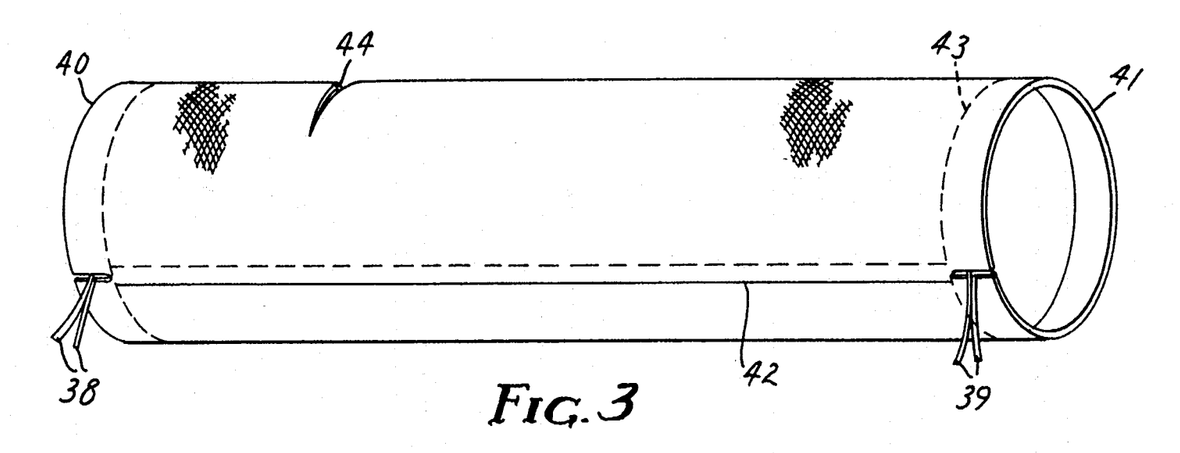
FIG. 3 is an isometric view of an alternative embodiment of the invention. This embodiment is a tubular covering for a short arm cast. The covering comprises drawstrings at the open ends to hold the open ends in place over the ends of the cast and maintain complete coverage of the cast during heat-shrinking.

FIG. 3 depicts a cover for a short arm cast. The cover comprises a rectangular sheet of nonwoven fabric formed into a tube with drawstrings 38 and 39 in place at the open ends 40 and 41. The drawstrings 38 and 39 are put in place on the rectangular sheet prior to forming the sheet into a tube. A string is laid parallel to, and about ¾ inch inside, an edge of the sheet which is to become one of the open ends of the tube. About ½ inch of the sheet along the length of the string is then folded back to cover the string. The terminal ¼ inch of the folded material is then sealed to the opposing surface of the sheet to form a seam 43 such that the string moves freely when the ends were pulled. This procedure is repeated on the opposite end of the sheet, and then the sheet is sealed lengthwise to form a seam 42 with about 3/16 inch overlap. In this embodiment, an appropriate slit 44 is cut in the side of the cover to accommodate the thumb which protrudes from the cast to be covered.

Figure 4:
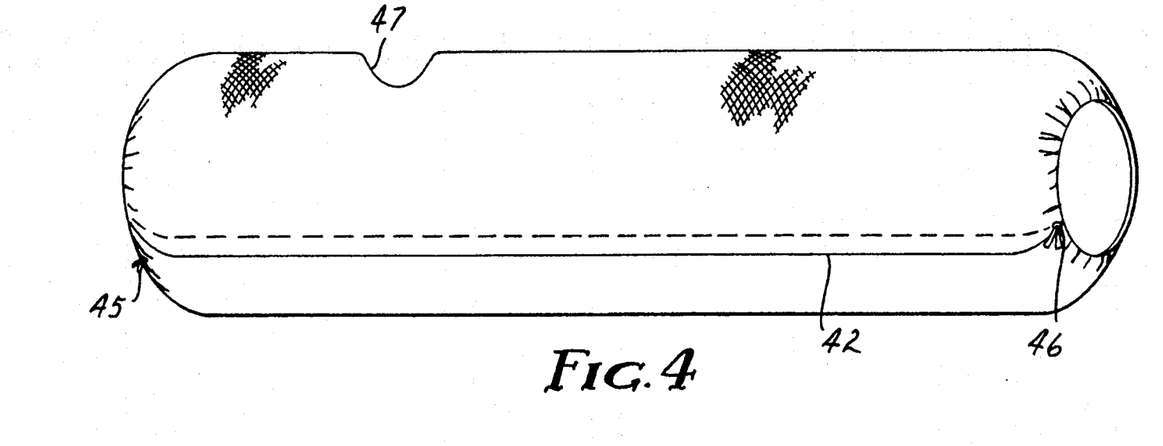
FIG. 4 is an isometric view of a further embodiment of the invention. This embodiment is a tubular covering for a short arm cast. The covering comprises elastic cuffs at the open ends to hold the open ends in place over the ends of the cast and maintain complete coverage of the cast during heat-shrinking.

FIG. 4 depicts a cover similar to that of FIG. 3, differing in that elastic bands 45 and 46 replace drawstrings 38 and 39, and thumbhole 47 is a hole of about 1 inch diameter.

The coverings of the invention are heat-shrinkable. Generally, polymeric materials are rendered heat-shrinkable by conversion to a dimensionally unstable state via molecular orientation through longitudinal stretching or biaxial stretching at an elevated temperature which is below the crystalline melting temperature of the polymer. Subsequent cooling provides heat-shrinkable material.

Many polymeric materials are suitable for forming the heat-shrinkable fibers of the nonwoven fabric used in the covering of the invention. These materials can be broadly categorized based on the mechanism of heat-shrinking which is operative in the preferred temperature range. One category includes materials with glass transition temperatures (Tg) within the range of 45° C. to 65° C. This group includes blends of polybutylene terephthalate and polyethylene terephthalate, polyethylene terephthalate copolymers, and polyester-polyether copolymers. A second category of materials are those materials with a broad melting range which extends down to about 60° C. to 70° C. This group includes ethylene copolymers such as ethylene/vinyl acetate copolymers, ethylene/acrylic acid copolymers, ethylene/propylene copolymers and blends thereof.

Materials preferred for the construction of invention are selected from those polymeric materials which have glass transition temperatures below 65° C., and preferably between 45° C. and 65° C. A material having too low a glass transition temperature will shrink prematurely at temperatures encountered during normal storage. On the other hand, a material having too high a glass transition temperature will require excessive temperature to effect shrinking, and discomfort or injury to the patient may result. At present, the most preferred polymeric material is PETG 5116, a copolymer of terephthalic acid, ethylene glycol, and diethylene glycol (available from Eastman Chemical Products, Inc., Kingsport, Tenn.).

The polymeric materials used in the coverings of the invention are converted to heat-shrinkable nonwoven webs. The degree of heat-shrinkability of nonwoven webs is determined for present purposes by cutting a 10 cm × 10 cm swatch of the web and laying it in a convection oven at a selected temperature for 1 minute. One dimensional shrinkage (shrinkage along one edge of the swatch) of at least 25 percent, and preferably at least 40 percent at 70° C. is desirable.

Preferably, the webs are melt-blown nonwoven webs of oriented fibers. Conventional processes for the preparation of melt-blown nonwoven webs may impart sufficient orientation to render the resultant webs sufficiently heat-shrinkable for present purposes. Spun-bond nonwoven webs may also be suitable. However the heat-shrinkability and repellent properties of the most preferred nonwoven webs are imparted as a result of preparation by a method which is disclosed in commonly assigned copending application U.S. Ser. No. 135,693, filed Dec. 21, 1987, which is incorporated herein by reference. In brief summary, the method comprises extruding fiber-forming polymeric material through the orifices of a die into a high-velocity gaseous stream where the extruded material is rapidly attenuated into fibers. The attenuated fibers are directed into the entrance of an elongated, flat chamber disposed near the die and extending in a direction parallel to the path of the attenuated fibers as they leave the die; air is blown into the chamber along the axis of the chamber at a velocity sufficient to maintain the fibers under tension during travel through the chamber. The fibers are collected after they leave the opposite end of the chamber.

Figure 5:
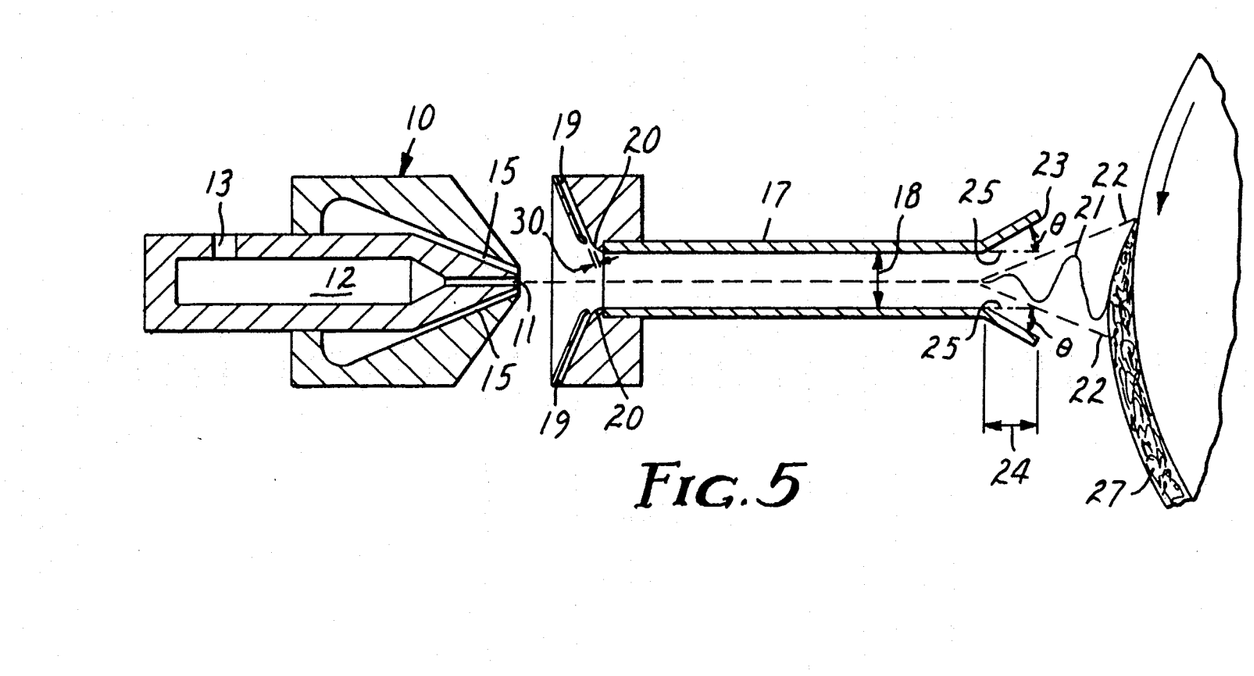
FIG. 5 is a cross sectional view of an apparatus suitable for preparing the preferred nonwoven web used in the coverings of the invention.

A representative apparatus useful for preparing the preferred oriented melt-blown fiber web is shown schematically in FIG. 5. Part of the apparatus, which forms the blown fibers, can be as described in Wente, Van A., "Superfine Thermoplastic Fibers" in *Industrial Engineering Chemistry*, Vol. 48, page 1342 et seq. (1956), or in Report No. 4364 of the Naval Research Laboratories, published May 25, 1954, entitled "Manufacture of Superfine Organic Fibers," by Wente, V. A.; Boone, C. D.; and Fluharty, E. L. This portion of the illustrated apparatus comprises a die 10 which has a set of aligned side-by-side parallel die orifices 11, one of which is seen in the sectional view through the die. The orifices 11 open from the central die cavity 12.

Fiber-forming material is introduced into the die cavity 12 through an opening 13 from an extruder (not illustrated). Orifices 15 disposed on either side of the row of orifices 11 convey heated air at a very high velocity. This air, called the primary air rapidly draws out and attenuates the extruded material into a mass of fibers.

From the melt-blowing die 10, the fibers travel to an orienting chamber 17. Generally, chamber 17 is flat and rectangular in cross section having a width somewhat greater than the width of the die 10, and a height (18 in FIG. 5) sufficient for the orienting air to flow smoothly through the chamber without undue loss of velocity, and for fibrous material extruded from the die to travel through the chamber without contacting the walls of the chamber (e.g., 5 to 20 mm, preferably 10 to 15 mm).

As shown in FIG. 5, the orienting chamber 17 is preferably flared at its exit end 23 to provide a more isotropic web. Flaring at an angle (the angle Θ) between a broken line 25 parallel to the central or longitudinal axis of the chamber and the flared side of the chamber between about 4° and 7° is believed ideal. Flaring lengths 24 between 25 centimeters and 75 centimeters have proven useful.

Orienting or secondary air is introduced into the orienting chamber through the orifices 19 arranged near the first open end of the chamber where fibers from the die enter the chamber. Air is preferably introduced from both sides of the chamber (i.e., from opposite sides of the stream of fibers entering the chamber) around curved surfaces 20. The fibers exiting from the melt-blowing die pass into the center of the chamber and travel lengthwise through the chamber. After they exit the chamber, they typically exhibit oscillating movement as represented by the oscillating line 21 and by the dotted lines 22 which represent the general outlines of the stream of fibers.

The orienting air enters the orienting chamber 17 at a high velocity. For most situations, velocities corresponding to pressures of about 70 psi (approximately 500 kPa) with a gap width for the orifice 19 (the dimension 30 in FIG. 5) of about 0.005 inches to 0.010 inches (0.013 cm to 0.025 cm), have been found optimum to assure adequate tension.

The chamber is preferably between about 30 and 120 centimeters in length. The entrance end of the chamber is generally within 5-10 centimeters of the die. After exiting from the orienting chamber 17, the solidified fibers are collected on the collector 26 as a web 27.

The strength and durability of the heat shrinkable non-woven webs used in the practice of this invention can be enhanced by embossing. Embossing is particularly desirable for oriented melt blown and spun-bonded fibrous webs which generally do not have the coherency of a collected web of conventional melt blown fibers. Embossing may be carried out thermally, ultrasonically or mechanically. Suitable embossing processes include placing a web on a patterned metal mesh screen and rolling with a heavy roller, passing a sheet through a nip using a heated (e.g., 50° C. to 70° C.) calendar roll and an engraved patterned embossing roll, ultrasonic bonding and other conventional embossing techniques. The preferred webs are embossed and exhibit superior durability, abrasion resistance and low linting.

Heat-shrinkable nonwoven webs of one or more layers are used in the coverings of the invention. Nonwoven webs of one or more layers will be permeable to air and other vapors. This permeability is variable according to the number of layers, thickness and the density of the web. It is optimal for the cover to be at least as permeable to air as is the underlying bandage, so that the cover does not provide a barrier to the escape of air and moisture from the underlying bandage. Accordingly, the covers of the invention exhibit an air permeability of at least 50 cc/sec and preferably at least 90 cc/sec, and most preferably at least 200 cc/sec when tested by the method described in Example 12 below.

It is desirable for the cover to have vapor permeability, air permeability, and water and soil repellent properties. This combination of properties is difficult to obtain with many nonwovens, especially those with high breathability, because their porosity tends to allow water to gradually soak in. This combination of properties, however, is readily obtained by treating the breathable coverings of the invention with fluorochemical or silicone based chemical repellents. The treatments may include spraying or otherwise applying the chemical treatment to the prepared covering material or, preferably, incorporating the chemical repellent in the starting formulation of molten polymer from which the nonwoven web is formed.

When the chemical repellent is incorporated into the formulation of molten polymer, the polymer pellets and a fluorochemical powder are dry blended and fed into the extruder. A suitable class of compounds for this purpose is the fluorochemical oxazolidinones disclosed in commonly assigned European Patent Office Publication Number 0260011 (Mar. 16, 1988) which is incorporated herein by reference. A preferred compound is the fluorochemical oxazolidinone of Formula I:

These fluorochemical oxazolidinones can be prepared using known organic reactions e.g., from the reaction of epoxides or halohydrins, e.g., chlorohydrins or bromohydrins, with organic isocyanates.

The preparation may be carried out stepwise by reacting the halohydrin with the isocyanate under urethane bond forming conditions, e.g., 20° C. to 100° C. for about 1 to 24 hours, to form a urethane intermediate, followed by addition of a base and reaction at about 20° C. to 100° C. for about 1 to 24 hours to form the oxazolidinone compositions. Alternatively, an epoxide can be reacted with an isocyanate in the presence of a catalyst, such as diethyl zinc, to form the oxazolidinone directly.

Fluorochemical formulations suitable for application to the already-formed webs include any of the fluorochemical formulations known to provide oil and water repellency to natural or synthetic fibers and films, for example the Scotchgard ® brand fabric protectors. These are available commercially from 3M Company and include formulations such as Scotchgard ® Fabric protector FC-214, Scotch-Release ® Brand Fabric Treatment FC-248, Scotchgard ® Brand Fabric Protector FC-324, 3M ® Brand Textile Chemical FC-461, 3M ® Brand Textile Chemical FC-210, 3M ® Brand Textile Chemical FC-828, 3M ® Brand fluorochemical formulations FC-393, FC-808 and FC-214B, Scotchgard ® Brand Rain and Stain Repeller FC-232 and the like. Alternate materials include Dupont's Soil Shedd ®, available from E. I. dupont de Nemours and Company, Wilmington, Del. It is presently preferred to use FC-214 or FC-232 formulations because they do not tend to yellow on the coverings and are known to be safe for use in proximity to skin.

Suitable silicones for use as low surface energy treatments include any of the silicones known to provide oil and water repellency to fibers and films. Silicones such as those available from Dow-Corning Corporation (e.g., C2-0563), and from General Electric Corporation (e.g., GE-SS4098), are suitable.

A disadvantage of these applied treatments is that, after application of the formulation, the cover is wet with solvent and must be dried. By virtue of the heat-shrinkability of the nonwoven web, however, rapid drying at an elevated temperature is complicated by the possibility of premature shrinkage. Thus, extended drying times at safe temperatures may be required when the treatment is applied to the web after the web is formed. This potential complication is avoided by incorporating the fluorochemical repellent into the molten resin prior to formation of the web as discussed above.

The active ingredient of the chemical treatment to impart low surface energy generally constitutes from 0.01 percent to 10 percent to the total weight of the covering, preferably 0.1 percent to 1.0 percent by weight of the total covering. It has been found that a surface energy of about 10 erg/cm$^2$ to 40 erg/cm$^2$ as measured by AATCC Test Method 118-1983 is sufficiently low to result in satisfactory water and soil repellent properties. A surface energy of less than 30 erg/cm$^2$ is preferred for the coverings of the invention.

Samples of covers of the invention were treated with 1.5 percent to 2.5 percent by weight total solids aqueous solutions of a fluorochemical repellent such as FC-214-30 (the designation 214-30 indicates that the formulation is supplied as 30 percent solids) by spraying the exterior until it appeared uniformly wetted. The cast cover was then dried by hanging in a convection oven at 110° F. (43° C.) for 30 minutes. The resulting surfaces repelled water.

The coverings of the invention can be formed from sheets or layers of the selected nonwoven web by pre-forming a shaped (e.g. cylindrical) covering or by custom fitting a covering to the object to be covered. Edges of a sheet of any shape can be joined by sonic-welding, heat-joining, sewing or suitable adhesives or adhesive tapes. Adhesives and adhesive tapes are particularly useful when custom fitting a covering. Sonic welding and heat joining are preferred for larger scale manufacturing of multiple units.

It may also be desirable to improve the fit of the covering of the invention by adhering or otherwise fastening an elastic material in the form of a band or cuff at the open ends of the cylindrical covering (for example, as shown in FIG. 4) so that the ends of the covering will stay in place during shrinking. Another method to hold the ends of a covering in place is to place drawstrings at the ends of the covering (as shown in FIG. 3) by a suitable method such as sewing, adhesives, adhesive tapes, sonic welding or heat sealing.

The webs from which the covering of the invention is made may be colored and/or embossed with a pattern for the purpose of providing an attractive covering. Accordingly, pigment may be added to the formulation from which the webs are formed, and the resulting colored webs may be embossed with a patterned embossing roll. Embossing also renders the webs more durable as described above.

The following Examples are provided to illustrate the invention but are not intended to limit the invention.

EXAMPLE 1

Polyethylene terephthalate (PET) with an intrinsic viscosity of 0.60 was dried in a dessicant oven and placed in the extruder of a conventional apparatus for the preparation of melt blown microfibers. A melt blown nonwoven web was prepared with the following extrusion conditions:

| | |
| --- | --- |
| orifices/cm: | 10 |
| primary air gap 15 | 0.063 cm |
| die temperature: | 310° C. |
| air temperature: | 320° C. |
| orifice 11 diameter: | 0.043 cm |
| collection distance: | 8 cm |

The resulting web had a basis weight of 32 g/m2.

EXAMPLE 2

A rectangular sheet (0.66 mm thick, 25.4 cm×30.5 cm) of nonwoven melt blown web from Example 1 was formed into a tube approximately 10 cm in diameter by heat sealing the lengthwise edges together with a thermal impulse heat sealing machine available from Vettrod Corporation at a heat setting of 2. The tube was placed over a short arm cast about 23 cm long. The cast had been prepared and cured according to the supplied directions from Scotchcast ® Plus brand casting tape (available from 3M Company, St. Paul, Minn.). The covering was then heated with a Master brand hot air gun Model HC-751A-15 held about 15 cm from the surface and set for about 50 percent air velocity. The temperature used was relatively high, about 70° C. to 90° C. The loosely fitting cover quickly shrank to a snug fit against the cast surface, producing a smooth finish that did not snag when cloth was rubbed over it. The covering was readily vapor permeable. The covering was removed easily by cutting with a scissors and replaced with a fresh covering.

EXAMPLE 3

Using the apparatus of FIG. 5, oriented microfibers were made from a glycol-modified polyester (PETG 5116 from Eastman Chemical Co.). The melt-blowing die was that of Example 1. The die temperature was 280° C. and the primary air temperature was 270° C.

Secondary air having a temperature of about 25° C. was blown into an orienting chamber 17 as shown in FIG. 5 at a pressure of 40 psi (276 kPa) through the orifices 19 shown in FIG. 5 having a gap width of about 0.005 inch (0.013 cm) to 0.010 inch (0.025 cm).

Fibers formed by the die 10 were drawn through orienting chamber 17 as shown in FIG. 5 having an interior height of 0.5 inch (1.3 cm), an interior width of 24 inches (61 cm), and a length of 18 inches (46 cm). The randomizing or expansion portion 24 of the chamber, illustrated in the drawing, was not present in the apparatus used in this Example.

The completed fibers exited the chamber and were collected on a screen-type collector spaced about 12 inches (30 cm) from the orienting chamber and moving at a rate of about 5 meters per minute. The resulting web of oriented microfibers was embossed with a 15 percent bond area star pattern at 63° C. and 30 psi to afford a web with a basis weight of 55 g/m2.

EXAMPLE 4

A matched pair of 0.43 mm thick sheets of oriented nonwoven melt blown microfibers were prepared according to the method of Example 3. The sheets were then made into a cast covering by heat sealing the sheets together using the heat sealing method of Example 2 with a heat setting of 0.5 to 1. The outside dimensions of the resulting covering shown in FIG. 1 were 56 cm on the longer straight sealed edge 32 and 36 cm on the opposite parallel edge 33, with a further sealed edge 31 tapering to the smaller open end 35 of the cover. The smaller open end 35 was 15 cm wide and the wider open end 36 was 23 cm wide.

The resulting tubular covering was placed over a short leg walker cast. The cast had been prepared and cured according to the supplied directions from Scotchcast ® Plus casting tape. The seam along the smaller end of the trapezoidal tube was centered along the bottom the foot portion of the cast. The ends of the tube were tucked inside the cast at each end and heat was applied with a Conair brand hair dryer, Model DN150; 1500 watts maximum; starting heat at the bottom in the rear, then heating the sides and finally heating the front and the top of the tube. The resulting covering fitted snugly around the entire cast as shown in FIG. 2.

EXAMPLE 5

PETG 5116 copolymer and a pigment concentrate were dry blended, extruded and melt-blown into an oriented nonwoven web using a process as described in Example 3, differing in the following extrusion conditions:

die temperature: 300° C.
primary air temperature: 295° C.

The resultant web was embossed with a 30 percent contact diamond pattern embossing roll at about 63° C. and 20 psi.

Using the method of Example 2 and webs prepared as described above, cylindrical coverings which were a medium blue and purple were successfully prepared, each from a 41 cm by 46 cm sheet, to accommodate a large short arm cast about 28 cm long with a maximum circumference of 33 cm. Each covering was fitted and heat-shrunk over an arm cast.

EXAMPLE 6

Using the method of Example 2, a tubular cast cover was prepared from a sheet of PETG 5116 nonwoven web (prepared according to Example 5). The outer surface of the cast cover was sprayed with an aerosol of 4 percent carbon dioxide, 21 percent 1,1,1-trichloroethane and 75 percent of a water and soil repellent mixture consisting of 10 percent FC-905 (available from 3M Company, St. Paul, Minn.), 10 percent n-butyl acetate and 80 percent 1,1,1-trichloroethane. The covering was air dried for 20 minutes, then placed over a short arm cast. The covering was then heat shrunk at a temperature of about 40° C. to 58° C. at the surface of the cast cover with a Conair dryer set at low heat and high air velocity. Water was run over the shrunken covering for about 15 seconds and was observed to bead up and run off the covering.

EXAMPLE 7

Two sheets of nonwoven web (prepared from Eastman 5116 copolymer according to the method of Example 5) were cut to a rectangular shape of 51/16 by 5⅜ inches (12.86 cm by 13.65 cm). One sheet was sprayed with a 2 percent aqueous solution of Scotchgard ™ brand Fabric Protector FC 214-30 (available from 3M Company, St. Paul, Minn.) and both the sprayed sheet and the untreated sheet were hung in a 112° F. (44° C.) oven for 15 minutes. The sheets were removed from the oven and shrunk using a Conair hair dryer set at a maximum air flow and heat. The untreated sheet shrank 84.2 percent and the treated sheet shrank 81.5 percent. Both shrinkages correspond to a one dimensional shrinkage of about 60 percent.

EXAMPLE 8

A cast covering (FIG. 3) was prepared from a 41 cm×46 cm sheet of nonwoven web of PETG 5116 copolymer (prepared according to the method of Example 5). The cover (as illustrated in FIG. 3) comprises the rectangular sheet of nonwoven web formed into a tube with drawstrings 38 and 39 in place at the open ends 40 and 41. To put the drawstrings in place on the rectangular sheet, a 22 inch (56 cm) string was laid parallel to and about ¾ inch inside an edge of the sheet which was to become an open end of the cover. About ½ inch of the sheet along the length of the string was then folded back to cover the string. The terminal ¼ inch of the folded material was then sealed to the opposing surface of the sheet with 3M brand No. 77 Spray Adhesive to form a seam such that the string moved freely when the ends were pulled. This procedure was repeated on the opposite end of the sheet, and then the length of the sheet was sealed to form a seam with about 3/16 inch (0.48 cm) overlap. A thumb hole was placed about 3 inches (7.6 cm) from the end of the resulting tubular covering by cutting a 2 inch slit. The outer surface was sprayed with a 2 percent aqueous solution of Scotchgard ™ brand Fabric Protector FC-214-30 until it appeared uniformly wet. The covering was dried in an oven at 110° F. (43° C.) for 30 minutes, then placed over an arm cast. The ends of the cover were manipulated into proximity with the ends of the cast and the drawstrings were tightened and tied at each end of the cast cover. The covering was then shrunk with a Conair dryer set at low heat and high air velocity to provide a temperature of 49° C. to 58° C. on the surface of the cast cover. The shrunken cover provided a smooth attractive surface on all parts of the cast. When a stream of water was passed over the cast the water did not penetrate or become absorbed by the covering.

EXAMPLE 9

A rectangular (40.5 cm by 46 cm) sheet of nonwoven web (PETG 5116, prepared according to Example 5) was embossed according to Example 5. A cast covering was prepared by a method similar to the method of Example 8, differing in that the seams and the ends of the cover encasing drawstrings were sealed by affixing one side of a double-sided adhesive tape, A-25 acrylic adhesive transfer tape Y9482 (available from 3M Company, St. Paul, Minn.), to one surface to be sealed and pressing the complimentary surface onto the second side of the double-faced tape. A thumb hole of about 1 inch (2.54 cm) diameter was cut about 3 inches (7.6 cm) from one end of the covering.

A second cast covering was prepared with the same dimensions, acrylic adhesive tape and nonwoven web as described above using a stretched and tied elastic band in place of the drawstring. A thumb hole was cut in this covering as described above (see FIG. 4).

Each of the above coverings was sprayed using a Preval sprayer, available from Precision Valve Corp., Yonkers, N.Y., with a 2 percent solution of FC-214-30 in water and the coverings were then dried in an oven at 110° F. (43° C.) for about 30 minutes.

A third covering was made using a 16 inch by 24 inch (41 cm by 61 cm) sheet of blue nonwoven web (PETG 5116, prepared and embossed as described in Example 5) by using a Branson ultrasonic sealer. The web was folded in half and passed between an ultrasonic "horn" and a rotating sealing wheel which provided a thin, strong seam. The cylinder was cut to 18 inches (46 cm) long and a thumb hole was cut in the same position as in the above coverings.

Each of the above three coverings was evaluated by placing them over a Scotchcast Plus ® cast on the arm of a volunteer. The ends of each of the first two covers were positioned at the ends of their respective casts, and the ends of the third cover were tucked into the ends of its cast. All three coverings were heat shrunk with a Conair hair dryer on low heat, high air velocity settings. All three fitted well, but the covering with the elastic bands fitted best, with essentially no wrinkles at the cast ends. The two casts covered by covers which were treated with FC-214-30 shed water very well when exposed to a stream of water from a faucet for 15 seconds.

EXAMPLE 10

In a 1 liter, 3-neck reaction flask fitted with a mechanical stirrer, condenser, gas inlet tube, thermometer, addition funnel and electric heating mantle were placed: 47.0 g (0.25 mole) m-xylylene diisocyanate, 50 g ethyl acetate solvent and 6 drops of dibutyl tin dilaurate catalyst. To this stirred mixture heated to 75° C. was added over a period of 2.5 hours under a slow nitrogen purge, a 50 weight percent ethyl acetate solution containing 297 g (0.5 mole) of $C_8F_{17}SO_2N(CH_3)CH_2CH(OH)CH_2Cl$ prepared from $C_8F_{17}SO_2N(CH_3)H$ and epichlorohydrin. Heating and stirring were continued for an additional 4 hours until substantially all of the isocyanate groups had been converted to urethane groups as determined by infrared absorption analysis. To this reaction mixture, cooled to room temperature (about 20° C.) and containing mainly the intermediate urethane product, was added with stirring a solution of 27.0 g (0.5 mole) of $NaOCH_3$ in 81 g methanol to effect cyclization of the urethane group and thereby formation of the oxazolidinone. The reaction mixture exothermed to 50° C. and this temperature was maintained with stirring for 5.5 hours. The reaction mixture was cooled to about 20° C., and the white solid product which formed during the course of the reaction was collected by filtration, washed once with 100 g ethyl acetate, twice with 100 g portions of deionized water and finally dried under water aspirator vacuum at 60° C. for 16 hours. Infrared and proton nmr analyses confirmed the product to be a fluorochemical 2-oxazolidinone having the structure:

EXAMPLE 11

A nonwoven web with a basis weight of 66 g/m² was prepared according to Example 3 using PETG 5116 dry blended with 1 percent by weight of the compound prepared in Example 10. The web was embossed with a 15 percent contact area weave pattern, at 65.5° C., 40 psi and 5.5 m/min. Two 8 ¼"×18" (21 cm×46 cm) rectangular sheets of this material were cut. A long edge of one sheet was overlapped by ¼" with a long edge of the other sheet. These edges were sealed together with A-25 acrylic transfer tape Y 9482. The remaining two long edges were similarly sealed together to form a tubular cover. A 2 inch slit was cut as in FIG. 3 to provide a thumb hole. The covering was placed over a Scotchcast TM Plus cast on the arm of a volunteer, with the ends of the covering extending about 1" beyond each end of the cast. A rubber band was slipped over each end of the covering to hold it against the limb at each end of the cast. The covering was then shrunk with a Conair hair dryer set at maximum. The resulting cover was smooth and well fitted to the surface of the cast, and it neither absorbed nor wicked water when water was poured over it for 15 sec.

EXAMPLE 12

Three 6"×16" (15.2 cm×40.6 cm) sheets were cut from cast covering material prepared according to Example 5. Each rectangular sheet was made into a tubular cover by overlapping the 6" edges by 1/4" and sealing them together with A-25 acrylic adhesive transfer tape Y9482. Each cover was then placed over a short arm cast, centered over the cast's smallest circumference (9¾", 24.8 cm), heat-shrunk as in Example 9 to form a smooth surface, and removed from the cast by cutting along the seam.

Each of these shrunken covers was tested for air permeability by placing the center section of the material between the upper and lower clamping plates of a Gurley densometer No. 4110 (with a circular orifice of 1 square inch), raising the lower plate to seal the material between the plates, freeing the inner cylinder (20 oz., 567.5 g) to sink, and measuring the time it took for the inner cylinder to drop a distance corresponding to the passage of 300 cc of air through the material. By this test, the material was found to have a mean air permeability of 300 cc/sec. When two layers of the material were placed in the densometer, the mean air permeability was 174 cc/sec. Three layers of material was found to pass 94 cc/sec.

The claimed invention is:

1. A covering for an orthopedic cast, which covering comprises a tubular nonwoven web of heat-shrinkable fibers adapted to fit loosely about the orthopedic cast and capable of being heat-shrunk to closely cover the orthopedic cast, wherein a 10 cm×10 cm piece of said covering shrinks at least 25 percent along one dimension when heated for one minute at 70° C.

2. A covering according to claim 1 wherein the fibers comprises material selected from the group consisting of blends of polybutylene terephthalate and polyethylene terephthalate; ethylene/vinyl acetate copolymers; ethylene/acrylic acid copolymers; polyethylene terephthalate copolymers; polyester-polyether copolymers; ethylene/propylene copolymers and blends thereof.

3. A covering according to claim 1 wherein the nonwoven web comprises oriented melt-blown fibers.

4. A covering according to claim 3 wherein the fibers comprise a copolymer of terephthalic acid, ethylene glycol and diethylene glycol.

5. A covering according to claim 1, wherein the covering is treated with a water and/or soil repellent.

6. A covering according to claim 5 wherein the treated covering exhibits a surface energy of less than about 40 erg/cm$^2$.

7. A covering according to claim 5, wherein the treated covering exhibits a surface energy of less than about 30 erg/cm$^2$.

8. A covering according to claim 5 wherein the repellent is a fluorochemical.

9. A covering according to claim 5 wherein the repellent is a silicone.

10. A covering according to claim 5 wherein the repellent comprises about 0.01 weight percent to 10 weight percent of the total weight of the covering.

11. A covering according to claim 5 wherein the repellent comprises about 0.1 weight percent to 1.0 weight percent of the total weight of the covering.

12. A covering according to claim 5 wherein the repellent is incorporated into the resin from which the fibers are formed.

13. A covering according to claim 5 wherein the repellent is applied to the nonwoven web after the web is formed.

14. A covering according to claim 12 wherein the repellent is a fluorochemical oxazolidinone.

15. A covering according to claim 14 wherein the oxazolidinone has the formula:

16. A covering according to claim 1 wherein the nonwoven web is capable of being heat-shrunk at a temperature below about 65° C.

17. A covering according to claim 1 wherein the web is capable of being heat-shrunk at a temperature between about 45° C. and about 60° C.

18. A covering according to claim 1 which comprises a tubular member having one or more open ends and elastic cuff means to hold the open ends in place during shrinking.

19. A covering according to claim 1 comprising a tubular member having one or more open ends and drawstring means to hold the open ends in place during shrinking.

20. A covering according to claim 1 wherein the nonwoven web is embossed.

21. A covering according to claim 1 wherein the nonwoven web has air permeability of at least 50 cc/sec.

22. A covering according to claim 1 wherein the nonwoven web has air permeability of at least 90 cc/sec.

23. A covering according to claim 1 wherein the nonwoven web has air permeability of at least 200 cc/sec.

24. A method of covering an orthopedic cast comprising the steps of:
  (i) placing over the orthopedic cast a covering comprising a nonwoven web of heat-shrinkable fiber adapted to fit loosely about the orthopedic cast and capable of being heat-shrunk to closely cover the orthopedic cast, wherein a 10 cm × 10 cm piece of said covering shrinks at least 25 percent along one dimension when heated for one minute at 70° C.; and
  (ii) heat shrinking the covering to closely cover the orthopedic cast.

25. A method according to claim 24 wherein the fiber comprises material selected from the group consisting of blends of polybutylene terephthalate and polyethylene terephthalate; ethylene/vinyl acetate copolymers; ethylene/acrylic acid copolymers; polyethylene terephthalate copolymers; polyester-polyether copolymers; ethylene/propylene copolymers and blends thereof.

26. A method according to claim 24 wherein the nonwoven web comprises oriented melt-blown fibers.

27. A method according to claim 24 wherein the web is capable of being heat-shrunk at a temperature below about 65° C.

28. A method according to claim 24 wherein said covering comprises a tubular member having one or more open ends and elastic cuff means to hold the open ends in place during shrinking and wherein said bandage is an orthopedic cast.

29. A method according to claim 24 wherein said covering comprises a tubular member having one or more open ends and drawstring means to hold the open ends in place during shrinking and wherein said bandage is an orthopedic cast.

30. A method according to claim 24 wherein the nonwoven web is embossed.

31. A method according to claim 24 wherein the nonwoven web has air permeability of at least 50 cc/sec.

32. A method according to claim 24 wherein the nonwoven web has air permeability of at least 200 cc/sec.

33. A method of covering a bandage comprising the steps of:
  (i) placing over the bandage a covering comprising a nonwoven web of heat-shrinkable fiber adapted to fit loosely about the bandage and capable of being heat-shrunk to closely cover the bandage, wherein the nonwoven web comprises oriented melt-blown fibers comprising a copolymer of terephthalic acid, ethylene glycol and diethylene glycol; and
  (ii) heat shrinking the covering to closely cover the bandage.

34. A method of covering a bandage comprising the steps of:
  (i) placing over the bandage a covering comprising a nonwoven web of heat-shrinkable fiber adapted to fit loosely about the bandage and callable of being heat-shrunk to closely cover the bandage, wherein the covering is treated with a water and/or soil repellent and exhibits a surface energy of less than about 40 erg/cm² and (ii) heat shrinking the covering to closely cover the bandage.

35. A method according to claim 34 wherein the repellent is a fluorochemical.

36. A method according to claim 35 wherein the fluorochemical is a fluorochemical oxazolidinone having the formula:

37. A method according to claim 34 wherein the repellent is a silicone.

38. A method according to claim 34 wherein the repellent comprises about 0.01 weight percent to 10 weight percent of the total weight of the covering.

* * * * *

UNITED STATES PATENT AND TRADEMARK OFFICE
CERTIFICATE OF CORRECTION

PATENT NO.: 5,439,438

DATED: August 8, 1995

INVENTOR(S): Dean A. Ersfeld, Timothy C. Sandvig, John F. Reed and Paul E. Hansen It is certified that error appears in the above-identified patent and that said Letters Patent is hereby corrected as shown below:

Col. 8, lines 25-26, "Vettrod" should read -- Vertrod --.

Col. 9, line 68, "51/16" should read -- 5-1/16 --.

Col. 14, line 67, "callable" should read -- capable --.

Signed and Sealed this

Eleventh Day of February, 1997

Attest:

BRUCE LEHMAN

Attesting Officer

Commissioner of Patents and Trademarks